(12) United States Patent
Rogan

(10) Patent No.: US 11,433,193 B2
(45) Date of Patent: Sep. 6, 2022

(54) DEVICE FOR HEATING A VAPOUR FORMING SUBSTANCE SUCH AS TOBACCO

(71) Applicant: JT International S.A., Geneva (CH)

(72) Inventor: Andrew Robert John Rogan, Forres (GB)

(73) Assignee: JT International S.A.

( * ) Notice: Subject to any disclaimer, the term of this patent is extended or adjusted under 35 U.S.C. 154(b) by 274 days.

(21) Appl. No.: 16/614,572

(22) PCT Filed: May 18, 2018

(86) PCT No.: PCT/EP2018/063129
§ 371 (c)(1),
(2) Date: Nov. 18, 2019

(87) PCT Pub. No.: WO2018/211084
PCT Pub. Date: Nov. 22, 2018

(65) Prior Publication Data
US 2020/0068953 A1 Mar. 5, 2020

(30) Foreign Application Priority Data
May 18, 2017 (EP) .................................... 17171741

(51) Int. Cl.
*A24F 13/00* (2006.01)
*A24F 17/00* (2006.01)
(Continued)

(52) U.S. Cl.
CPC ............. *A61M 15/06* (2013.01); *A24F 40/40* (2020.01); *A24F 40/46* (2020.01); *A24F 40/465* (2020.01);
(Continued)

(58) Field of Classification Search
CPC .......... A24F 40/20; A24F 40/40; A24F 40/46; A24F 40/465; A24F 40/50; A61M 11/042; A61M 15/06
See application file for complete search history.

(56) References Cited

U.S. PATENT DOCUMENTS 5,053,176 A * 10/1991 Cameron ................ B29B 7/603
264/173.17
5,479,948 A 1/1996 Counts et al.
(Continued)

FOREIGN PATENT DOCUMENTS

EP 2989912 A1 3/2016
JP H07147965 A 6/1995
(Continued)

OTHER PUBLICATIONS

International Search Report including Written Opinion for Application No. PCT/EP2018/063129, dated Oct. 12, 2018, pp. 1-15.

*Primary Examiner* — Abdullah A Riyami
*Assistant Examiner* — Thang H Nguyen
(74) *Attorney, Agent, or Firm* — Lerner, David, Littenberg, Krumholz & Mentlik, LLP

(57) ABSTRACT

A device for heating a vapour forming substance includes a compartment for receiving a vapour forming substance. The compartment is divided into plural regions. A heater is provided for heating a vapour forming substance in the compartment in use to generate vapour therefrom. The device further includes means for controlling the heater such that a region adjacent to the heater can be selectively heated and so that vapour from that selectively heated region passes out from the device during operation of the heater. The heater extends in the longitudinal direction of the compartment.

22 Claims, 5 Drawing Sheets

(51) Int. Cl.

| | | |
|---|---|---|
| *A24F 25/00* | (2006.01) | |
| *A61M 15/06* | (2006.01) | |
| *A61M 11/04* | (2006.01) | |
| *A24F 40/40* | (2020.01) | |
| *A24F 40/46* | (2020.01) | |
| *A24F 40/465* | (2020.01) | |
| *A24F 40/50* | (2020.01) | |
| *A24F 40/20* | (2020.01) | |

(52) U.S. Cl.
 CPC ........... *A24F 40/50* (2020.01); *A61M 11/042* (2014.02); *A24F 40/20* (2020.01)

(56) References Cited

U.S. PATENT DOCUMENTS

| | | | | |
|---|---|---|---|---|
| 5,649,554 | A * | 7/1997 | Sprinkel | A24F 40/465 |
| | | | | 131/194 |
| 6,053,176 | A * | 4/2000 | Adams | A24F 40/53 |
| | | | | 131/329 |
| 9,357,803 | B2 * | 6/2016 | Egoyants | F16L 59/065 |
| 9,554,598 | B2 * | 1/2017 | Egoyants | H05B 3/44 |
| 10,863,770 | B2 * | 12/2020 | Mironov | A24F 40/42 |
| 10,869,504 | B2 * | 12/2020 | Mironov | A24F 40/42 |
| 10,888,123 | B2 * | 1/2021 | Silvestrini | A24F 40/42 |
| 2015/0083149 | A1 * | 3/2015 | Oglesby | A24F 42/60 |
| | | | | 261/143 |
| 2017/0071250 | A1 | 3/2017 | Mironov et al. | |
| 2017/0079326 | A1 | 3/2017 | Mironov | |
| 2018/0169357 | A1 * | 6/2018 | Reevell | A24F 40/42 |
| 2018/0228216 | A1 * | 8/2018 | Saygili | A61M 11/042 |
| 2018/0310622 | A1 * | 11/2018 | Mironov | A24D 1/20 |
| 2020/0068953 | A1 * | 3/2020 | Rogan | A61M 11/042 |

FOREIGN PATENT DOCUMENTS

| | | |
|---|---|---|
| JP | 2014520542 A | 8/2014 |
| JP | 2016528874 A | 9/2016 |
| JP | 2016529874 A | 9/2016 |
| WO | 2013034458 A1 | 3/2013 |
| WO | 2016120344 A2 | 8/2016 |
| WO | 2017068100 A1 | 4/2017 |

* cited by examiner

DEVICE FOR HEATING A VAPOUR FORMING SUBSTANCE SUCH AS TOBACCO

CROSS-REFERENCE TO RELATED APPLICATIONS

The present application is a national phase entry under 35 U.S.C. § 371 of International Application No. PCT/EP2018/063129, filed May 18, 2018, published in English, which claims priority to European Patent Application No. 17171741.6, filed May 18, 2017, the disclosures of which are incorporated herein by reference.

BACKGROUND OF THE INVENTION

The present invention relates to a device for heating a vapour forming substance such as tobacco.

In recent times it has become popular to provide an alternative to traditional tobacco-based products such as cigarettes and in which vapour is generated to provide flavoured vapour to a user without needing to burn the tobacco.

In this field a number of different types of devices have been proposed, including those that heat up flavoured liquid and those which heat tobacco and pass air over the heated tobacco to generate the flavoured vapour.

With the latter type of device one approach has been to provide a rod of tobacco, similar in shape to a cigarette, and then to heat the rod to generate the vapour. This has advantages in terms of the ease of understanding of operation for a user, as well as simplicity of construction. However, it can be difficult to produce such a device at an acceptable cost to a consumer as there is a need for the provision of an effective heater which does not require a large power supply. Furthermore, it can be difficult with such devices to ensure a consistency of quality in the vapour delivery to the user as air is drawn in through the rod of tobacco and passes over the entire length of the rod meaning that the vapour generated later on in the use of the device has to pass over tobacco which has already been exposed to earlier vapour. This can result in a change in flavour over time and use of the individual rod which is difficult to control.

BRIEF SUMMARY OF THE INVENTION

The present invention therefore seeks to provide a device for heating tobacco which is of low cost, which has efficient heating, and yet which has reliable and predictable vapour generation to improve a user's experience.

According to the present invention there is provided a device for heating a vapour forming substance, the device comprising a compartment for receiving vapour forming substance in use, the compartment being divided into plural regions; and a heater for heating tobacco in the compartment in use to generate vapour therefrom, wherein the device further comprises means for controlling the heater and the regions such that a region adjacent to the heater can be selectively heated and so that vapour from that selectively heated region passes out from the device during operation of the heater, wherein the heater extends in the longitudinal direction of the compartment.

With the device of the present invention it is possible to control the heating in a region of the vapour forming substance to improve heater efficiency and therefore power consumption. Furthermore, control of the heating to a specific region in the compartment enables greater control of vapour generation and the avoidance of air passing over all vapour forming substance that may be in the device in use, improving vapour quality and therefore user experience.

The device may further comprise means for generating relative motion between the heater and the regions such that a region can be placed adjacent to the heater to be selectively heated and so that vapour from that selectively heated region passes out from the device during operation of the heater, and wherein the heater is positioned around a portion of the outer periphery of the compartment.

The device, alternatively, may comprise several heaters and controls these heaters selectively.

The heater may be an inductive heater and may be an induction coil around the periphery of the compartment. In this case the device may further comprise an electromagnetic shield positioned between the induction coil and the compartment, the shield being arranged to define a gap through which electromagnetic radiation can pass from the induction coil to the compartment in use. The shield may be formed from a ferrite. The shield may be rotatable to control the selection of the region to be heated.

The device may be arranged to receive a rod-shaped portion of vapour forming substance in the compartment and a divider may be positioned within the compartment to define the plural regions so that only a select region of, for example, a rod-like tobacco portion may be heated and have air pass through it at any one time. This results in a simple mechanism which is simple to use while ensuring a high quality of vapour production.

The divider may comprise an electromagnetic shielding material (e.g. copper, ferrite or some combination thereof) such that, when an inductive heater is employed, only one selected region is heated and heating of the other regions is prevented.

If a divider is provided it may be rotatable to provide the relative movement between the heater and the regions and arranged such that it moves vapour forming substance by rotating it around a longitudinal axis of the compartment. The divider may be structured such that it can receive a rod of vapour forming substance inserted into the compartment in the longitudinal direction of the rod and may be arranged such that it rotates within a cross-sectional area which is smaller than that of the cross-sectional area of the rod such that when a portion is inserted any wrapper on the outer periphery of the portion passes around the divider. This prevents the portion coming apart and improves handling for a user.

The divider may have a longitudinal length which is at least 50% and more preferably 80% of the length of a portion of vapour forming substance that can be received. This can ensure that an air route is defined in a simple and effective manner.

The device may have a retaining member for retaining the portion of vapour forming substance on the device in use. This ensures reliable retention and positioning of the portion on the device.

The device may further comprise an inlet which restricts airflow through the compartment to a selected region which corresponds to a region adjacent to a heater such that, in use, air passes substantially only over the region of a compartment which is being heated to control vapour generation. This isolates the route through which air passes in a simple and effective manner.

The present invention also provides a system for heating a vapour forming substance which comprises the above-mentioned device in any of its configurations in conjunction with means for providing air to the compartment, means for driving the means for generating relative motion, and a power supply for providing power to the heater and to the driving means, together with a control of controlling the power supply means for driving and optionally also the heater. The system may further comprise tobacco. The device and system may be arranged to receive a rod of tobacco which has formed on one end a mouth piece through which a user draws vapour through in use. In the case of the device comprising an inductive heater the system may comprise tobacco with susceptor material therein such that the inductive heater heats the susceptor material in use. The susceptor may comprise one or more, but not limited, of aluminium, iron, nickel, stainless steel and alloys thereof, e.g. nickel chromium.

The susceptor material may comprise groups of components each of which are heated by exposure to electromagnetic radiation at differing wavelengths, with each group being positioned in its own region within the vapour generating substance such that in use each said region can be heated selectively. With this arrangement the device may comprise an inductive heater arranged to operate at plural different selectable frequencies so as to allow, in use, selective separate heating of each region of the substance.

The vapour forming substance may be any suitable substance capable of forming a vapour. The substance may comprise plant derived material and in particular, the substance may comprise tobacco. Typically, the vaporisable substance is a solid or semi-solid tobacco substance. This allows the susceptor to be held in position within the body so that heating is able to be provided repeatably and consistently. Example types of vapour generating solids include powder, granules, pellets, shreds, strands, porous material, foam or sheets.

Preferably, the vaporisable substance may comprise an aerosol-former. Examples of aerosol-formers include polyhyrdric alcohols and mixtures thereof such as glycerine or propylene glycol. Typically, the vaporisable substance may comprise an aerosol-former content of between approximately 5% and approximately 50% on a dry weight basis. Preferably, the vaporisable substance may comprise an aerosol-former content of approximately 15% on a dry weight basis.

Also, the vaporisable substance may be the aerosol-former itself. In this case, the vaporisable substance may be liquid. Also, in this case, the body may have a liquid retaining substance (e.g. a bundle of fibres, porous material such as ceramic, etc.) which retains the liquid to be vaporized by the vaporizer such as a heater and allows a vapour to be formed and released/emitted from the liquid retaining substance towards the air outlet for inhalation by a user.

BRIEF DESCRIPTION OF THE DRAWINGS

An example of the present invention will now be described with reference to the accompanying drawings, in which.

DETAILED DESCRIPTION

Figure 1:
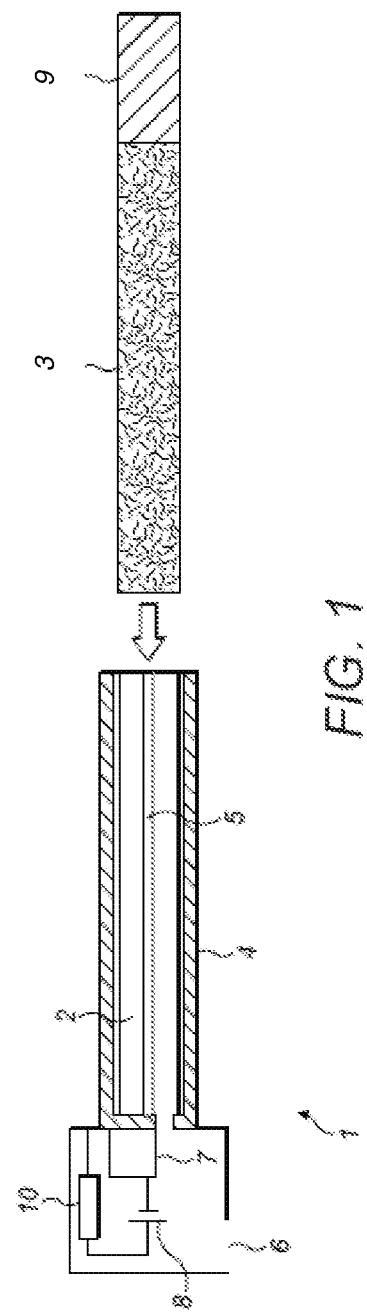
FIG. 1 is a side cross-sectional view of a system according to the present invention.

Referring to FIG. 1, the side cross-sectional view of a device 1 according to the present invention is shown. The device 1 has an outer housing and defines a compartment 2 which, in this example, is generally cylindrical with a circular cross-section. Around a portion of the outer periphery of the compartment 2 is positioned a heater 4 and positioned within the compartment 2 is a rotating divider 5, which is, in this example, aligned along the longitudinal axis of a compartment 2. One end of the compartment 2 is open such that it can receive a rod of vapour forming substance, for example tobacco 3 in the axial direction of the compartment, the direction shown by the arrow. In use, a user inserts a rod of tobacco 3 which is split between regions defined by the outer periphery of the compartment 2 and the arms of the divider 5. In this example it is split in to four regions, although it will be appreciated that there could be more than four regions or indeed less than four regions, although there should be at least two.

At the end of the compartment 2 opposite to the opening there is defined an aperture, aligned with the heater 4, which generally has a cross-section which is of similar shape to one of the regions defined by the divider 5. The divider may be formed so that it prevents air from passing therethrough and thereby defines a particular air channel as will be described in more detail below. The aperture passes through to an inlet 6 such that air can be drawn from the inlet 6 through the aperture and through the compartment and out through a mouth piece 9 at one end of the rod 3 when a rod 3 has been inserted into the compartment 2.

The device 1 further comprises a driving mechanism 7, which may be a manual drive mechanism which may have a indexing mechanism to ensure rod 3 is turned by a predetermined correct angle each time (for example 90 degrees). In this case however the driving mechanism is a motor 7 which is powered by a power source 8, such as a battery, which may be rechargeable. The motor 7 can drive the divider 5 to rotate it around the longitudinal axis of the compartment 2. The power source 8 may also provide power to the heater 4 and a controller 10 is provided to control the application of power both to the heater 4 and the motor 7 to control the interrelationship between operation of the heater 4 and the divider 5 in use, as will be described below.

Figure 2:
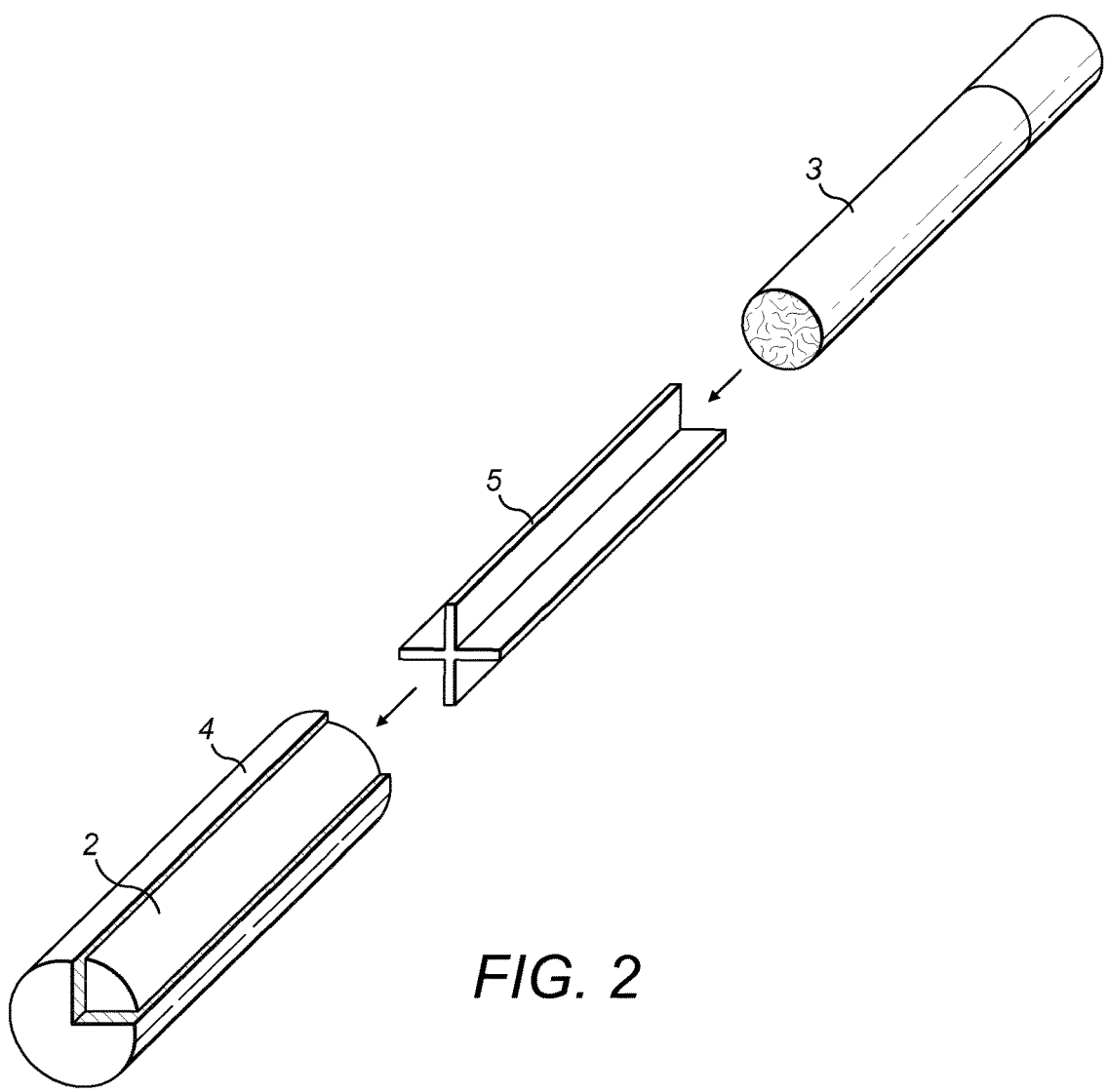
FIG. 2 is a side perspective expanded view of some of the components of the system of FIG. 1.

FIG. 2 shows an expanded view of some of the components of the device 1 of FIG. 1. Here the location of the heater around a portion of the compartment 2 can be seen, together with the structure of the divider 5 and the rod 3.

Figure 3:
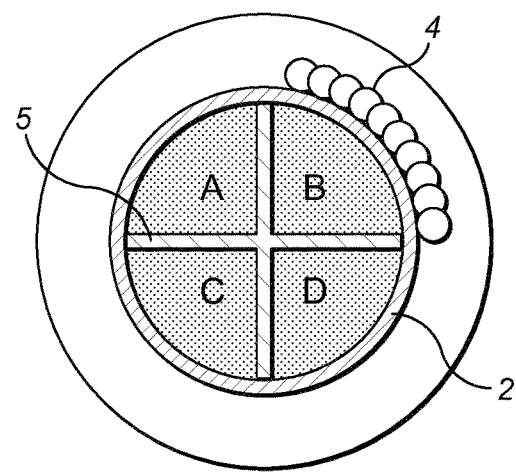
FIG. 3 is a cross-sectional view of a system according to the present invention with regions within a compartment labelled A to D.
Figure 5A:
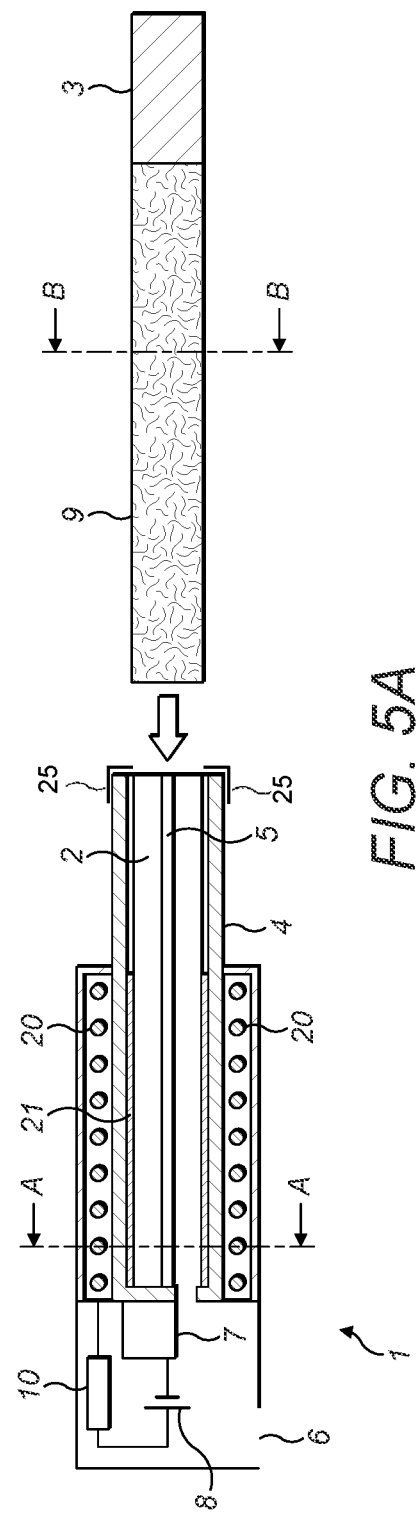
FIGS. 5A and 5B are views of further examples of a system according to the present invention.
Figure 5B:
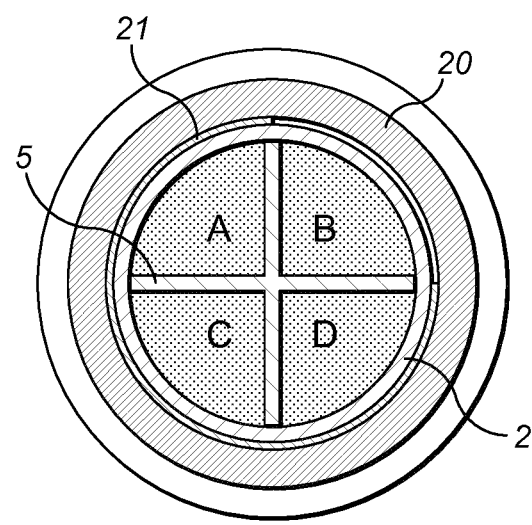

Referring to FIG. 3 a schematic cross-sectional view of a device 1 according to the present invention is shown in which the relative positions of the heater 4, compartment 2 and a rod 3 inserted in the compartment 2 can be seen from one end. The position of the divider 5 within the compartment 2 can be seen and from which it can be understood that, when a rod 3 has been inserted, the divider 5 defines the tobacco within the rod 3 generally into four regions A, B, C, D within the compartment 2. Referring to FIG. 5A, an alternative device according to the present invention is provided in which components that correspond to those of the example of FIG. 1 are numbered identically. However, as can be seen from this example, an alternative heating arrangement is provided in the form of an induction coil 20. Whilst the induction coil may comprise any suitable material, typically the induction coil may comprise a Litz wire or a Litz cable. The induction coil may be divided into four separately actuatable quarters or, as is shown in this example and represented in FIG. 5B, may be employed in combination with a shield 21, which in this example is formed from a ferrite that extends around three quarters (i.e. 270°) of the outer periphery of the compartment 2 between the compartment 2 and the induction coil 20. In a yet further example no shield is present but the induction coil is arranged to operate at plural separate frequencies and associated control circuitry enables selection of the frequency as required during operation.

Figure 6A:
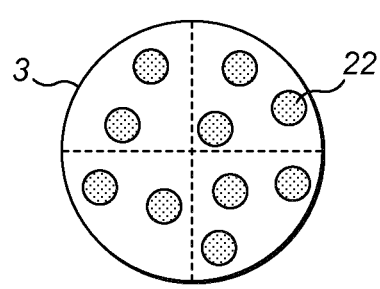
FIGS. 6A and 6B are cross sectional views of example rods of vapour generating substance that may be employed with the example systems of FIGS. 5A and 5B
Figure 6B:
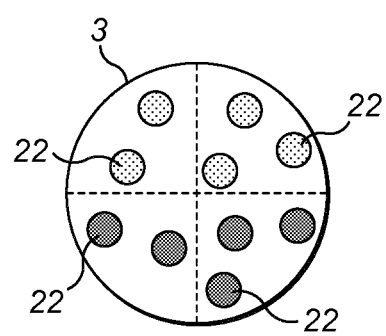

In these examples, shown in FIGS. 6A and 6B, the tobacco rod 3 has susceptor material impregnated in it. That material may be in the form of strips or particles and is arranged to be distributed evenly within the tobacco of the rod 3 as shown in FIG. 6A. In an alternative example, shown in FIG. 6B, the rod has susceptor material of different types in different regions thereof, each susceptor type arranged to heat up as a different exciting electromagnetic frequency. This example is used in combination with a device where the induction coil 20 can operate at different selectable frequencies such that each region of the rod 3 can be selectively heated separately.

The susceptor in any example may comprise one or more, but not limited, of aluminium, iron, nickel, stainless steel and alloys thereof, e.g. nickel chromium. With the application of an electromagnetic field in its vicinity, the susceptor may generate heat due to eddy currents and magnetic hysteresis losses resulting in a conversion of energy from electromagnetic to heat.

In these examples the power source and circuitry may be configured to operate at a high frequency. Preferably, the power source and circuitry may be configured to operate at a frequency of between approximately 80 kHz and 500 kHz, preferably approximately 150 kHz and 250 kHz, more preferably approximately 200 kHz. The coil assembly may be arranged to operate in use with a fluctuating electromagnetic field having a magnetic flux density of between approximately 0.5 Tesla (T) and approximately 2.0 T at the point of highest concentration.

As with the earlier example, a divider 5 may be provided, although this is not essential. In this example, if such a divider 5 is provided there can be benefits in it being formed from material that can form an electromagnetic shield such as copper, ferrite or some combination thereof. It will be appreciated that any of the additional features of the example device of FIG. 1 can be incorporated into that of FIG. 5 and vice versa.

Figure 4A:
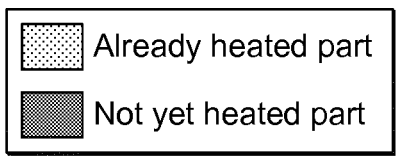
FIGS. 4A to 4D are schematic diagrams showing one aspect of the operation of a system according to the present invention in use.
Figure 4A:
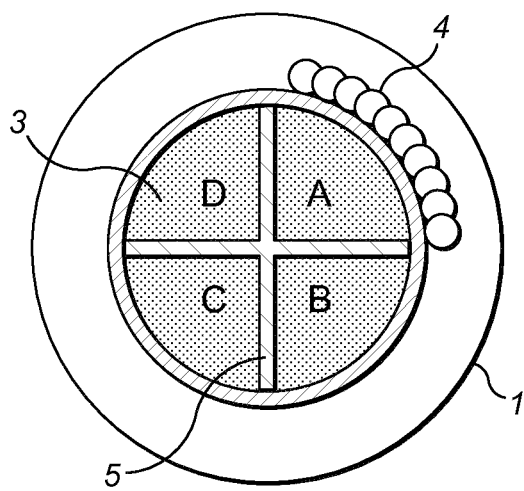

With any of the above example devices, once a user has inserted the rod 3 the device 1 is ready for use. The user then activates the device 1 and the controller 10 activates the application of power to the heater 4 such that region A only is heated directly by the heater 4. This is shown in FIG. 4A. The user then draws on the mouth piece 9 and air is drawn through the inlet 6, in the compartment 2 at the end opposite to the mouth piece 9, such that it is drawn only through the region A, heated with the tobacco in the region A and vapour generated.

Figure 4B:
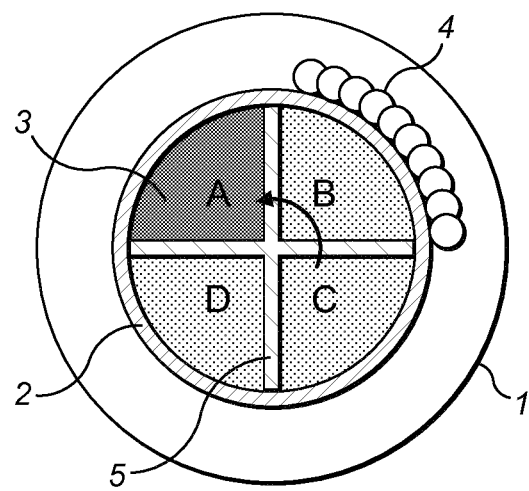
Figure 4C:
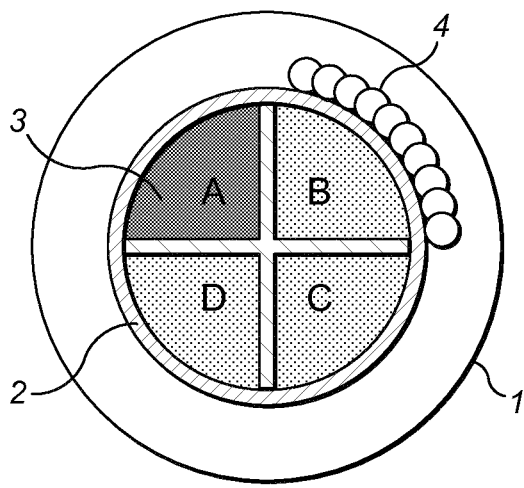
Figure 4D:
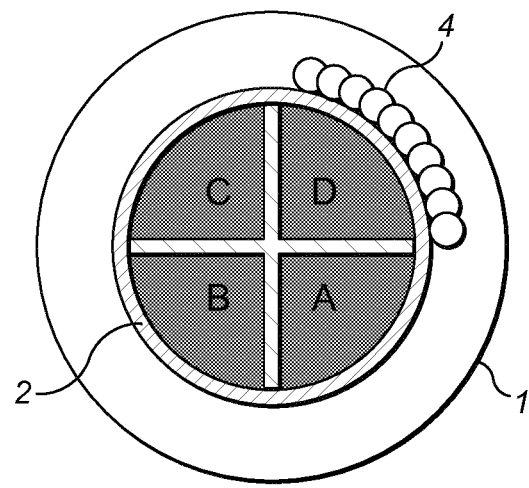

After sufficient use of the tobacco in the compartment A, as determined by the user, or by the device itself through monitoring of the amount of time the device has been used with the tobacco in region A in place, the device operates to rotate the divider 5. This rotation may, again, be under the control of the user, or may be automated through determination of certain parameters of use by the device itself. Rotation of the divider 5 moves the region A away from being directly adjacent to the heater 4 and moves a further region B into the position that region A once held. This is shown in FIG. 4B. The tobacco in region A is now considered to be used, but the device can then, under operation of the user, use the heater 4 to heat the tobacco in region B for subsequent vapour generation, as shown in FIG. 4C. Once it has been determined that the tobacco in region B has been used, in accordance with the similar process to that for region A, further rotation through other regions C, D can be performed, as shown in FIG. 4D until it is considered that all of the tobacco within the rod 3 and held within the compartment 2 has been used. At this point an indication may be provided to a user and further use of the device may be restricted until the rod 3 has been removed and a fresh rod 3 inserted. After insertion of a fresh rod 3 the device 1 can of course be used again.

Referring to the example of FIGS. 5A to 6B, there are a number of possible adaptations to the operation described above. In one possible configuration where no divider 5 is provided the shield 21 can be rotated through the regions A to D in the manner described above in relation to FIGS. 4A to 4D. Each region is exposed to heating by the induction coil 20 exciting the susceptor material 22 in the tobacco rod 3, with excitation only passing into the region adjacent to the opening in shield 21. Alternatively, if four inductor sections are provided, then each can be activated independently in a manner equivalent to that described in respect of FIGS. 4A to 4D. As a further alternative, the shield 21 can be fixed, and the divider 5 operated to rotate to provide an operation as shown in FIGS. 4A to 4D and described above. In any of these options heating occurs by excitement of the susceptor material, which can have benefits over a more conventional heating arrangement as described above in that it controls more specifically the heating of the material and prevents excessive heating of the casing device which may improve safety. As will be understood, in the example where the rod 3 had regions with different susceptor material in each then the operation is generally the same as for the other examples but with control of the operating frequency of the induction coil 20 selecting which region is heated at any point during operation. With this arrangement the shield 21 and a divider 5 (especially rotating and shielding function) is optional but may be provided to control air flow.

A retaining mechanism, such as a clip or biased retainer member 25 as shown in FIG. 5A, may be provided to retain the rod 3 securely within the compartment 2. In such an arrangement it may only be under a specific manual operation of the user that the rod 3 can be removed. Furthermore, it can be beneficial to choose quite specifically the relative dimensions of the divider 5, compartment 2 and rod 3, to ensure ease of insertion of the rod 3 yet adequate division of tobacco in the rod 3 between the regions defined by the divider 5 and the compartment 2. For example, it may be appropriate for the divider 5 to be sized to provide a narrow gap between its outer edges and the inner surface of a wrapper on the outer surface of the rod to enable ease of insertion and passage of the wrapper on the rod 3, which retains the tobacco in place, through that narrow gap.

It will also be appreciated that for safety and other reasons the controller 10 of the device 1 may be configured to prohibit excessive use of any individual rod 3 by providing a usage time limit on that rod 3. Furthermore means may be provided within the device 1 such that the rod 3 is altered during its removal so that cannot be reinserted to ensure quality of flavour delivery and restrict reuse.

As will be appreciated from the above, the present invention provides a device for heating tobacco which is simple to operate and yet which has improved flavour delivery characteristics over the prior art arrangements by providing more localised and controlled heating of tobacco within the device when it is being used. It also enables flavoured delivery from a single rod of similar dimensions to those used in the prior art to be improved by localising passage of air over tobacco in the rod in use to improve flavour characteristics and consistency.

The invention claimed is:

1. A device for heating a vapour forming substance, the device comprising:
   a compartment for receiving the vapour forming substance in use, the compartment extending along a longitudinal direction and being divided into plural regions;
   a heater for heating a vapour forming substance in the compartment in use to generate vapour therefrom, wherein the heater extends in the longitudinal direction of the compartment;
   a controller for controlling the heater such that a region of the plural regions that is adjacent to the heater can be selectively heated and so that vapour from that selectively heated region passes out from the device during operation of the heater; and
   a driving mechanism or a motor for generating relative motion between the heater and the regions such that one of the regions can be placed adjacent to the heater to be selectively heated and so that vapour from that selectively heated region passes out from the device during operation of the heater.

2. The device according to claim 1, wherein the heater is positioned around a portion of an outer periphery of the compartment.

3. The device according to claim 1, wherein the heater comprises an induction coil.

4. The device according to claim 1, further comprising a rod-shaped portion of vapour forming substance in the compartment.

5. The device according to claim 1, further comprising a clip or a biased retainer member for retaining a portion of vapour forming substance on the device in use.

6. The device according to claim 1, further comprising an air inlet positioned to provide air substantially only into one of the regions of the compartment adjacent to the heater.

7. A system for heating a vapour forming substance comprising:
   the device according to claim 1;
   an inlet for allowing air to enter the compartment;
   a power supply for the heater; and
   a controller for controlling the power supply.

8. The system for heating a vapour forming substance according to claim 7, further comprising a portion of vapour forming substance positioned in the compartment and a mouthpiece extending out from the device.

9. A system for heating a vapour forming substance comprising:
   the device according to claim 1;
   an inlet for allowing air to enter the compartment;
   a power supply for the heater; and
   a controller for controlling the motor and the power supply,
   wherein the motor is configured for driving the driving mechanism for generating relative motion.

10. The system for heating a vapour forming substance according to claim 9, further comprising a portion of vapour forming substance positioned in the compartment and a mouthpiece extending out from the device.

11. A system for heating a vapour forming substance, comprising:
    the device according to claim 1;
    a portion of vapour forming substance positioned in the compartment; and
    a mouthpiece extending out from the device.

12. A device for heating a vapour forming substance, the device comprising:
    a compartment for receiving the vapour forming substance in use, the compartment extending along a longitudinal direction and being divided into plural regions;
    a heater for heating a vapour forming substance in the compartment in use to generate vapour therefrom, wherein the heater extends in the longitudinal direction of the compartment, wherein the heater comprises an induction coil;
    a controller for controlling the heater such that a region of the plural regions that is adjacent to the heater can be selectively heated and so that vapour from that selectively heated region passes out from the device during operation of the heater; and
    an electromagnetic shield positioned between the induction coil and the compartment, the electromagnetic shield being arranged to define a gap through which electromagnetic radiation can pass from the induction coil to the compartment in use.

13. The device according to claim 12, wherein the electromagnetic shield is rotatable about the compartment.

14. The device according to claim 12, wherein the electromagnetic shield extends around three quarters of an outer periphery of the compartment.

15. A device for heating a vapour forming substance, the device comprising:
    a compartment for receiving the vapour forming substance in use, the compartment extending along a longitudinal direction and being divided into plural regions;
    a heater for heating a vapour forming substance in the compartment in use to generate vapour therefrom, wherein the heater extends in the longitudinal direction of the compartment;
    a controller for controlling the heater such that a region of the plural regions that is adjacent to the heater can be selectively heated and so that vapour from that selectively heated region passes out from the device during operation of the heater; and
    a divider positioned within the compartment to define the plural regions.

16. The device according to claim 15, wherein the divider is constructed to prevent the passage of air therethrough.

17. The device according to claim 15, further comprising a motor for generating relative motion between the heater and the regions such that one of the regions can be placed adjacent to the heater to be selectively heated and so that vapour from that selectively heated region passes out from the device during operation of the heater, wherein the divider is rotatable by the motor.

18. The device according to claim 17, wherein an end of the compartment defines an aperture to allow air to pass through the selectively heated region.

19. The device according to claim 18, wherein the aperture has a cross-section that corresponds to a cross-section of one of the regions defined by the divider.

20. The device according to claim 15, further comprising a rod-shaped portion of vapour forming substance in the compartment, wherein the divider is arranged to spread across a cross-sectional area which is smaller than that of the portion of vapour forming substance such that when the portion of vapour forming substance is inserted into the compartment, any wrapper on the outer periphery of the portion passes around the divider.

21. The device according to claim 15, further comprising a rod-shaped portion of vapour forming substance in the compartment, wherein the divider has a longitudinal length which is at least 50% of a length of the portion of vapour forming substance.

22. The device according to claim 15, wherein the divider comprises an electromagnetic shielding material.

\* \* \* \* \*